US 9,723,881 B1

(12) United States Patent
Bauman

(10) Patent No.: US 9,723,881 B1
(45) Date of Patent: Aug. 8, 2017

(54) HEAD AND FACIAL PROTECTIVE DEVICE

(71) Applicant: April Surgical Products, LLC, Traverse City, MI (US)

(72) Inventor: Kristin C. Bauman, Traverse City, MI (US)

(73) Assignee: April Surgical Products, LLC, Traverse City, MI (US)

( * ) Notice: Subject to any disclaimer, the term of this patent is extended or adjusted under 35 U.S.C. 154(b) by 0 days.

(21) Appl. No.: 15/136,039

(22) Filed: Apr. 22, 2016

Related U.S. Application Data

(63) Continuation-in-part of application No. 14/078,004, filed on Nov. 12, 2013, now abandoned.

(60) Provisional application No. 62/152,539, filed on Apr. 24, 2015.

(51) Int. Cl.
  *A61F 5/37* (2006.01)
  *A41D 13/11* (2006.01)

(52) U.S. Cl.
  CPC ...... *A41D 13/1107* (2013.01); *A41D 13/1161* (2013.01); *A61F 5/3707* (2013.01)

(58) Field of Classification Search
  CPC ...... A61F 5/3707; A61F 5/05883; G21F 3/02; A41D 13/11; A41D 13/1107; A41D 13/1146; A41D 13/1184; A61G 13/121; A61G 13/1215
  USPC ...................... 128/857, 859, 870; 2/206, 424
  See application file for complete search history.

(56) References Cited

U.S. PATENT DOCUMENTS

| | | | |
|---|---|---|---|
| 3,337,883 A | 8/1967 | Duncan | |
| D271,834 S | 12/1983 | Huntsinger | |
| 4,504,050 A | 3/1985 | Osborne | |
| 4,550,713 A | 11/1985 | Hyman | |
| D298,992 S | 12/1988 | Voss | |
| 5,269,035 A | 12/1993 | Hartunian | |
| 5,848,448 A | 12/1998 | Boyd | |
| 6,112,333 A * | 9/2000 | Mazzei | A61G 13/12 128/857 |
| D456,516 S | 4/2002 | Cheshaek et al. | |
| 6,490,737 B1 | 12/2002 | Mazzei et al. | |
| 6,637,058 B1 | 10/2003 | Lamb | |
| 6,842,924 B1 | 1/2005 | Walters | |
| D625,420 S | 10/2010 | Sharps et al. | |
| D665,912 S | 8/2012 | Skripps | |
| 8,234,731 B2 | 8/2012 | Skripps | |
| 2004/0078869 A1 * | 4/2004 | Bell | A41D 13/1161 2/206 |

(Continued)

*Primary Examiner* — Kari Rodriquez
*Assistant Examiner* — Kari Petrik
(74) *Attorney, Agent, or Firm* — Gardner, Linn, Burkhart & Flory, LLP

(57) ABSTRACT

A protective device for protecting the face and/or head of an individual receiving medical treatment in a face upward position includes a face portion having an exterior surface, an interior surface, and an aperture extending from the exterior surface to the interior surface, and includes a pair of opposed flexible side portions extending outwardly from the face portion. The face portion is configured to be positioned about the face of an individual with at least a portion of the individual's face exposed by the aperture, and the side portions are configured to be wrapped around and completely surround the head of the individual whereby the individual's head is supported on at least one of the side portions when the individual is receiving medical treatment in a face upward position.

19 Claims, 13 Drawing Sheets

(56) References Cited

U.S. PATENT DOCUMENTS

| | | | |
|---|---|---|---|
| 2009/0151049 A1* | 6/2009 | Conrardy | A42B 5/00 |
| | | | 2/206 |
| 2011/0036358 A1* | 2/2011 | Mattalino | A61F 7/02 |
| | | | 128/857 |
| 2015/0128960 A1 | 5/2015 | Bauman | |
| 2015/0181951 A1* | 7/2015 | Kaforey | A61B 19/2203 |
| | | | 128/845 |

* cited by examiner

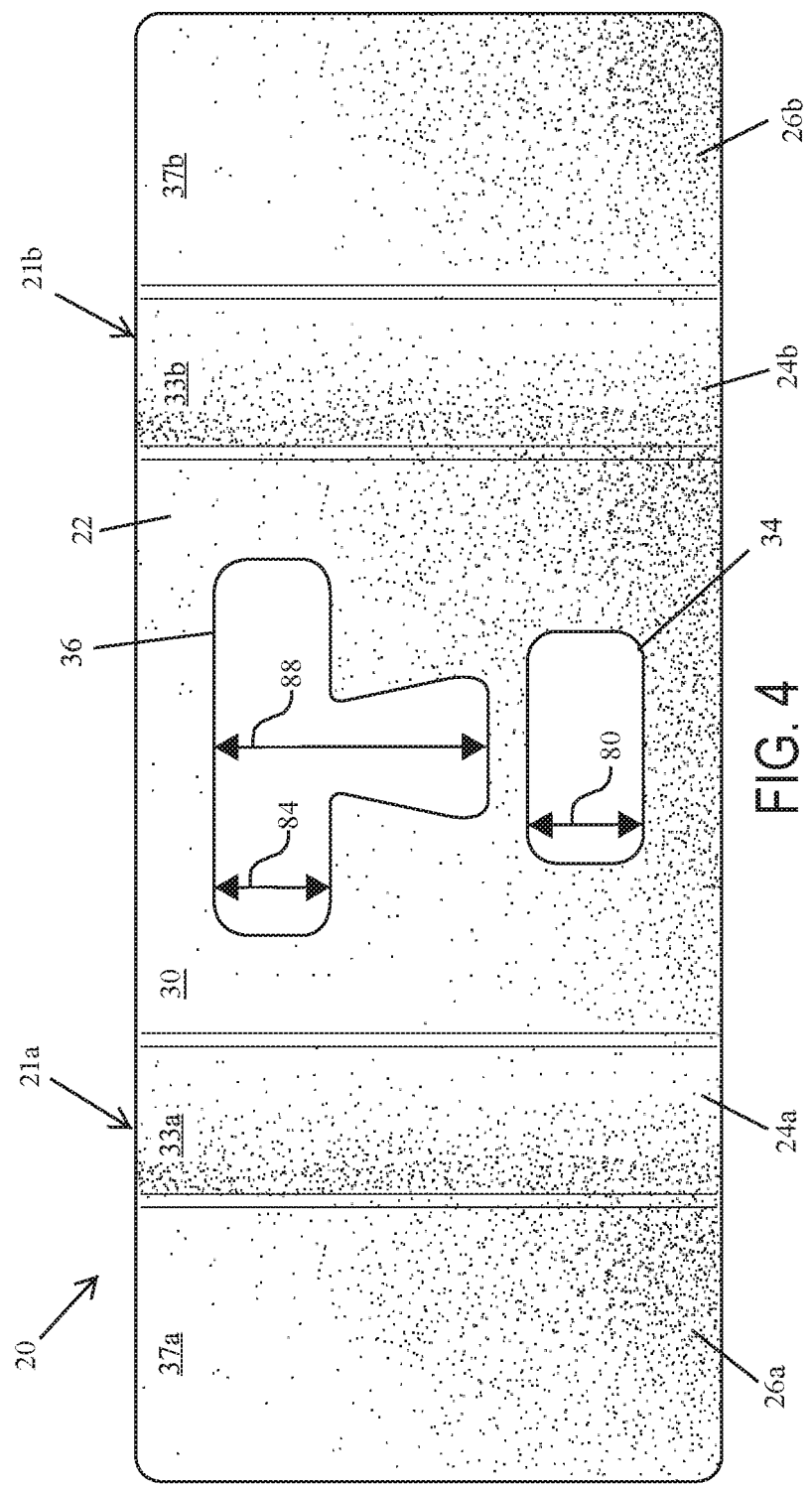

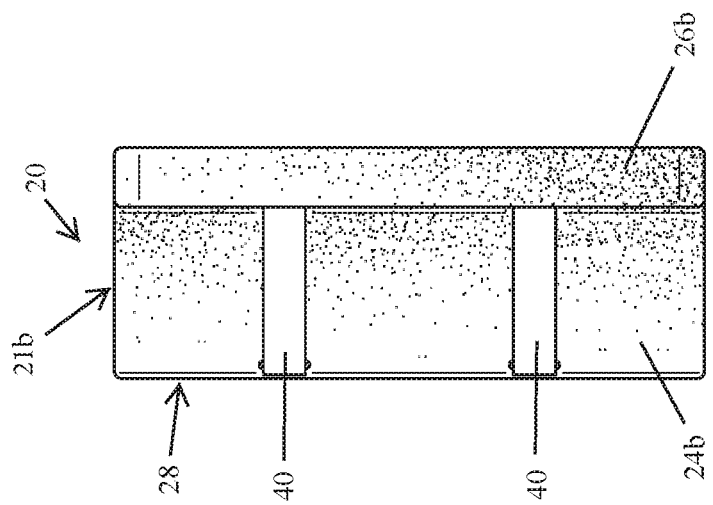
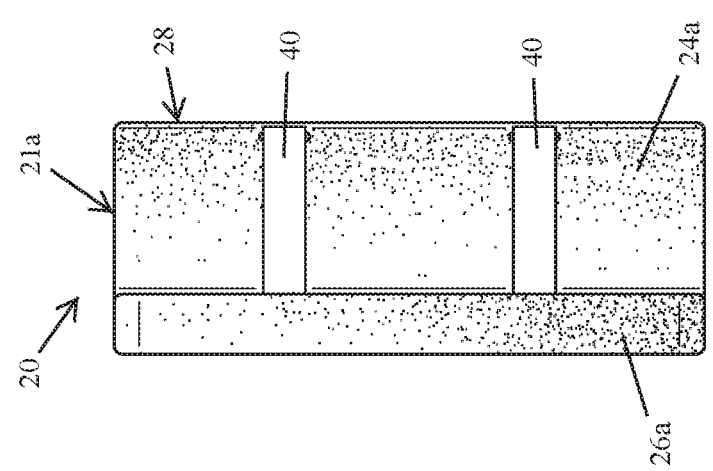

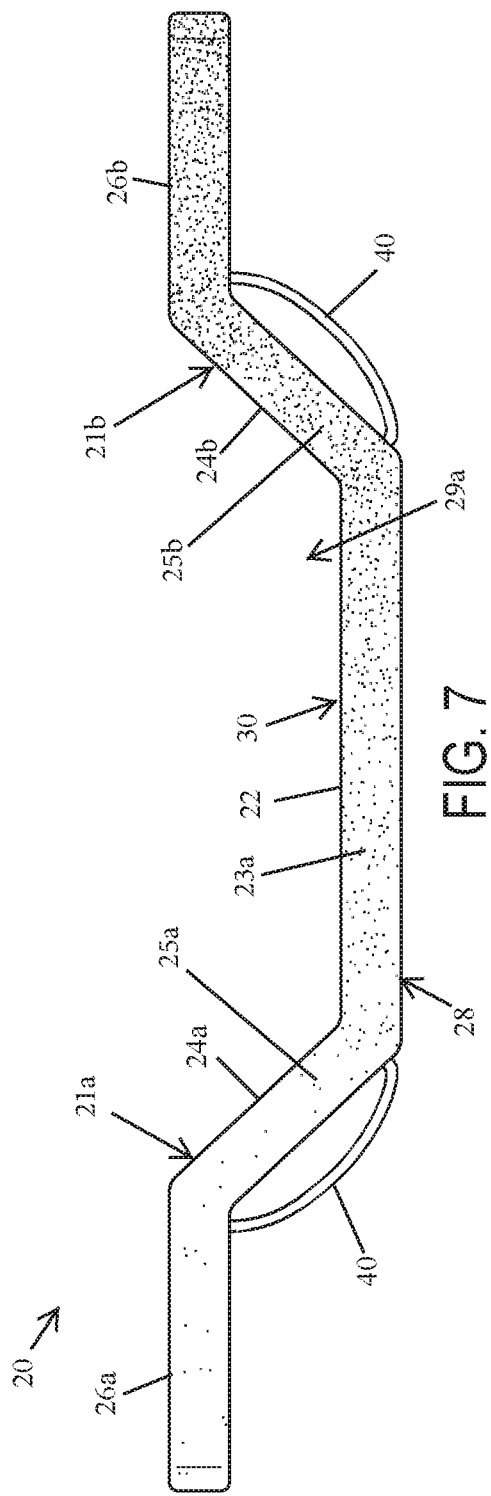
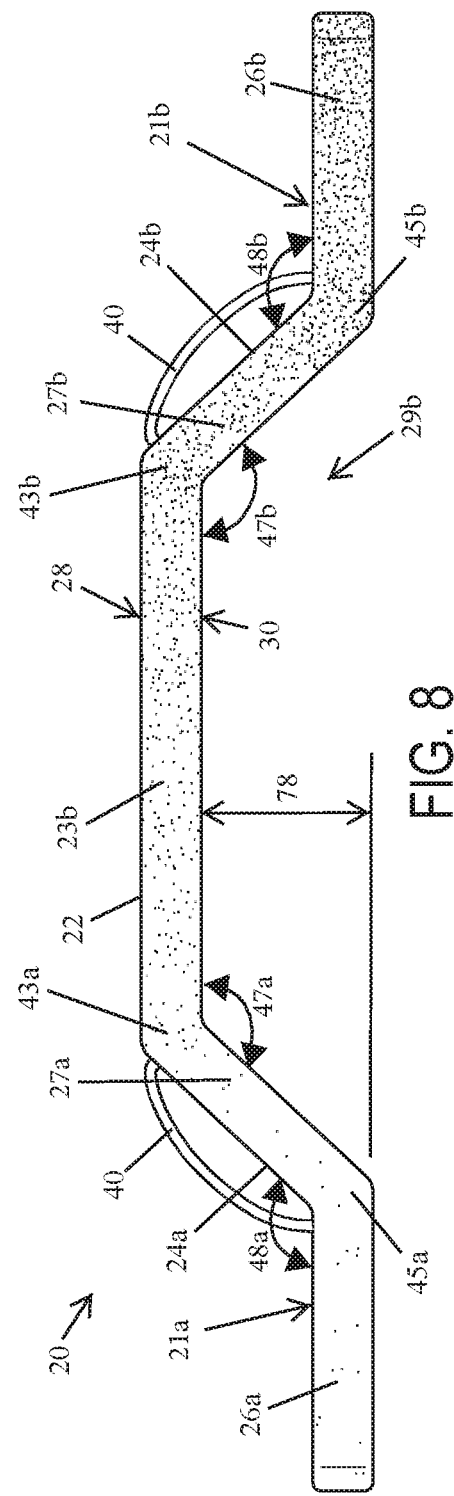

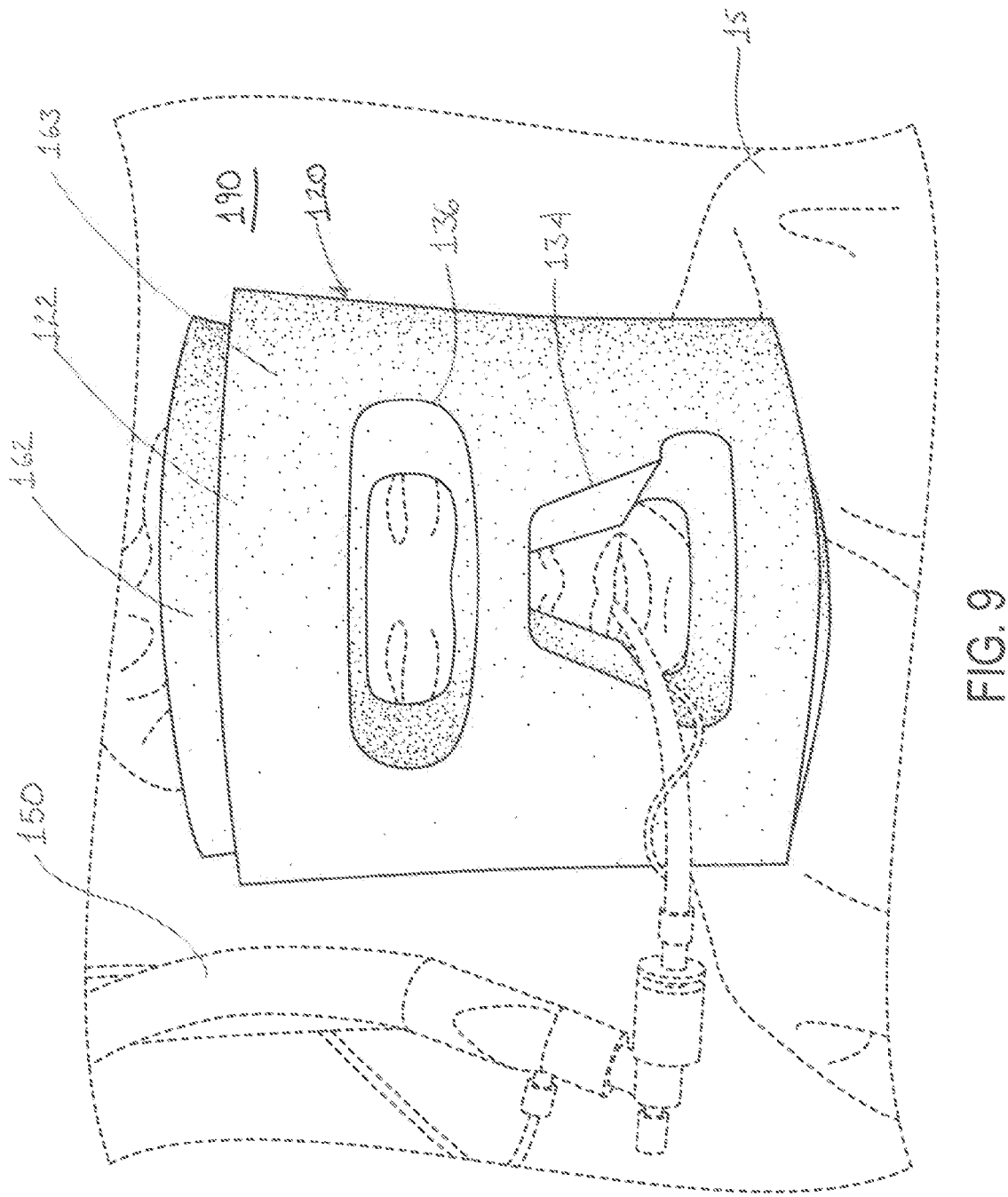

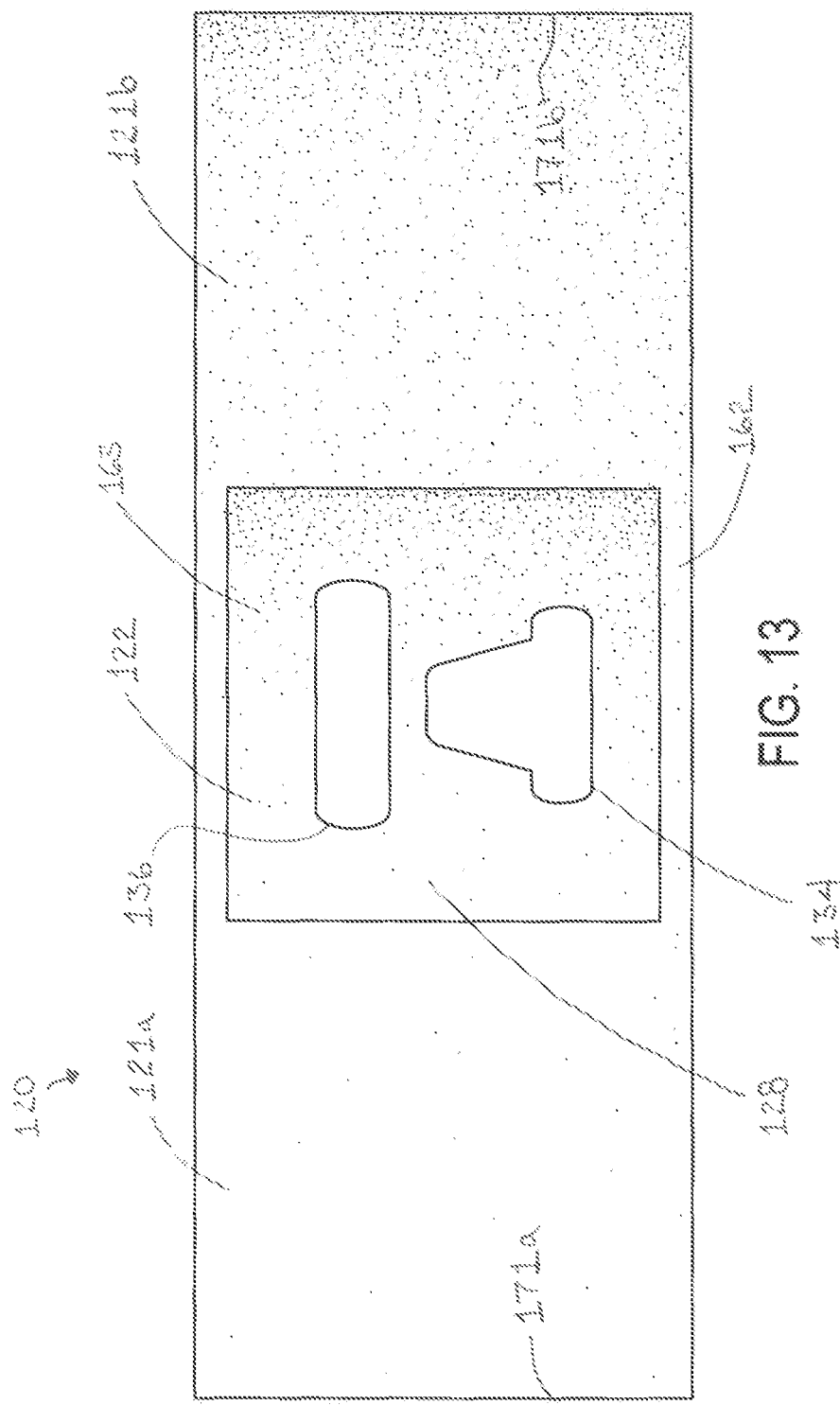

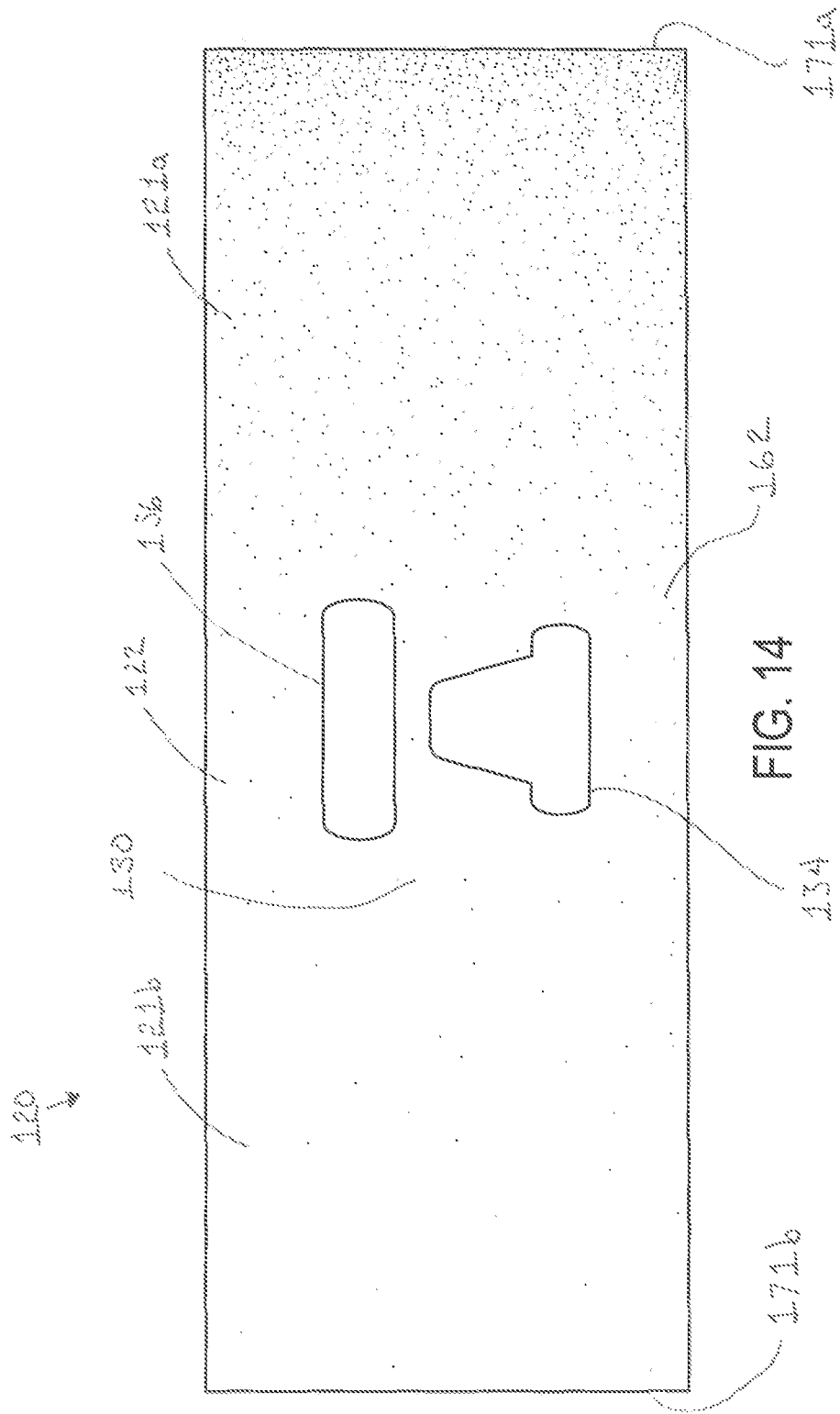

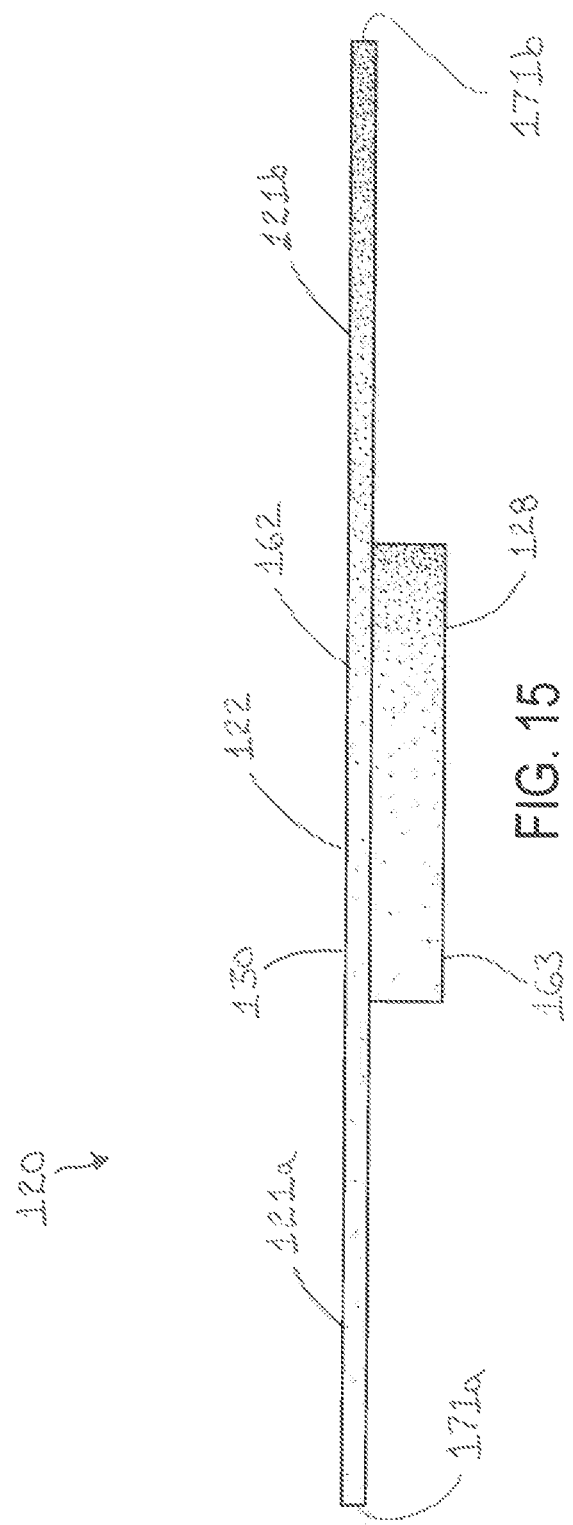

HEAD AND FACIAL PROTECTIVE DEVICE

CROSS REFERENCE TO RELATED APPLICATION

The present application is a continuation-in-part of U.S. nonprovisional application Ser. No. 14/078,004, filed Nov. 12, 2013, for HEAD AND FACIAL PROTECTIVE DEVICE, and claims priority of U.S. provisional application Ser. No. 62/152,539, filed Apr. 24, 2015, which are hereby incorporated herein by reference in their entireties.

BACKGROUND AND FIELD OF THE INVENTION

The present invention is directed to a protective device and, more particularly, to a method and apparatus for protecting the head and/or face of a patient lying in the supine position.

Protecting a patient's face during surgery is an important concern. Unintentional pressure on the ocular structures can cause severe damage and even blindness. Uneven pressure on the face can lead to decreased blood flow, potentially resulting in nerve damage. Compression injuries to the forehead, nose, ears, cheeks, and mouth can also occur. Once a patient undergoing a surgical procedure is fully anesthetized under a general anesthetic, the patient is no longer able to move in response to an uncomfortable or painful stimulus. Therefore, constant vigilance by the anesthesia provider is necessary to protect the vital facial structures.

SUMMARY OF THE INVENTION

The present invention provides a device and method for protecting the face and/or head of an individual receiving medical treatment in a face up, or supine, position.

According to an aspect of the present invention, a protective device for protecting the face and/or head of an individual receiving medical treatment in a face upward or supine position comprises a face portion having an exterior surface, an interior surface, and an aperture extending from the exterior surface to the interior surface, and includes a pair of opposed flexible side portions extending outwardly from the face portion. The face portion is configured to be positioned about the face of an individual with at least a portion of the individual's face exposed by the aperture, with the side portions configured to be wrapped around and completely surround the head of the individual whereby the individual's head is supported on at least one of the side portions when the individual is receiving medical treatment in a face upward position.

In particular embodiments the face portion comprises a top layer and a separate base layer, where the side portions and base layer may comprise a unitary member formed of the same material. Both the top and base layers may be constructed of foam, and in particular embodiments the top layer may be constructed of a foam that is firmer or stiffer than the foam of the base layer. Still further, for example, the top layer may be constructed to be thicker than the base layer, such as with the top layer being at least approximately twice as thick as the base layer. The top layer and base layer may be adhesively affixed together.

The side portions each include an end, with the ends configured to be engaged together, such as in abutting orientation, when the side portions are wrapped about the head of an individual. In a particular embodiment the side portions are of substantially similar length with respect to each other such that they extend equally from the face portion. Still further, the face portion may comprise a pair of apertures, with one of the apertures configured to expose an individual's eyes and the other aperture configured to expose the individual's nose and mouth.

According to another aspect of the present invention, a method of protecting the face and/or head of an individual receiving medical treatment in a face upward position includes providing a protective device comprising a face portion having an exterior surface, an interior surface, and an aperture extending from the exterior surface to the interior surface, with the protective device further comprising a pair of opposed flexible side portions extending outwardly from the face portion. The method further includes positioning the face portion about the face of an individual with at least a portion of the individual's face exposed by the aperture, and wrapping the side portions around the head of the individual to completely surround the head of the individual whereby the individual's head is supported on at least one of the side portions when the individual is receiving medical treatment in a face upward position.

In particular embodiments of the method, the provided protective device comprises a top layer and a separate base layer with the side portions and base layer comprising a unitary member formed of the same material. Still further, both the top and base layer may be constructed of foam with the top layer being firmer than the base layer.

The protective device and method of using the protective device of the present invention provide protection for a patient undergoing surgery in the supine position by allowing forces to be directed away from the sensitive areas of the face and cranial region, while providing a light weight device by way of the flexible foam construction, which promotes the prevention of injury to a patient that may result from contact with a stiffer and/or heavier protective device. The apparatus and method of the present invention also help to keep the patient's head from falling to the side, further reducing the risks of decreased blood flow and possible nerve damage. The apparatus and method, therefore, provide increased protection over conventional practices.

These and other objects, advantages, purposes and features of the present invention will become more apparent upon review of the following specification in conjunction with the drawings.

BRIEF DESCRIPTION OF THE DRAWINGS

FIG. 4 is a bottom plan view of the protective device of FIG. 2;

FIG. 5 is a left elevation view of the protective device of FIG. 2;

FIG. 6 is a right elevation view of the protective device of FIG. 2;

FIG. 7 is a top end elevation view of the protective device of FIG. 2;

FIG. 8 is a bottom end elevation view of the protective device of FIG. 2;

FIG. 9 is an alternative embodiment of a facial and head protective device in accordance with the present invention shown in use on a patient;

FIG. 13 is a top plan view of the protective device of FIG. 10;

FIG. 14 is a bottom plan view of the protective device of FIG. 10; and

FIG. 15 is a side elevation view of the protective device of FIG. 10.

DESCRIPTION OF THE PREFERRED EMBODIMENTS

Figure 1:
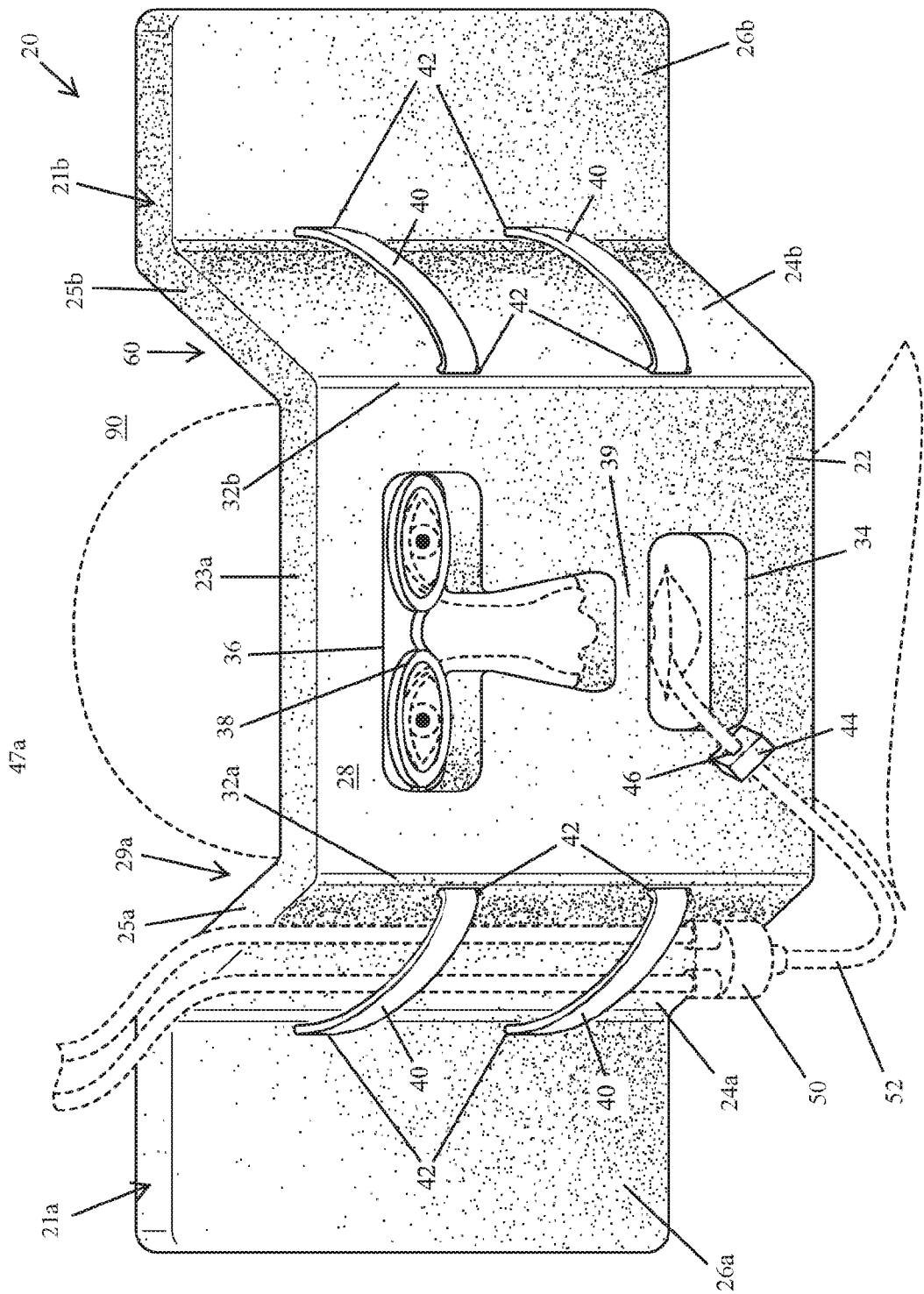
FIG. 1 is a top perspective view of a facial and head protective device in accordance with the present invention shown in use on a patient.

The present invention will now be described with reference to the accompanying figures, wherein the numbered elements in the following written description correspond to like-numbered elements in the figures. Referring to FIG. 1, a facial and head protective device 20 comprises a face portion or a central member 22 and a pair of side legs or portions 21a, 21b extending from opposite sides of central member 22, with member 22 also including apertures 34 and 36. Together, side portions 21a, 21b and member 22 define a recessed area or cavity 60 for receiving the head of a patient lying in a supine position when protective device 20 is placed over or about the patient's head and the distal ends of side portions 21a, 21b contact a bed, gurney, pillow, or other support surface 90 on each side of the patient's head. When so arranged apertures 34 and 36 are aligned with the patient's eyes, nose and mouth. Protective device 20 is adapted to direct forces applied thereto, such as from medical equipment or the like, to the support surface 90 to thereby protect the patient. Moreover, in the illustrated embodiment protective device 20 comprises a soft, foam-type padding that cushions the patient's face, protects pressure points, and may engage the patient's facial structures to aid in preventing shifting of protective device 20 during medical procedures, such as surgeries and the like.

In the illustrated embodiment the side legs 21a, 21b of protective device 20 include side members 24a and 24b and corresponding base elements or members 26a and 26b, respectively. Side members 24a and 24b extend downward from generally opposite sides 32a and 32b of member 22. Base members 26a and 26b extend outward and away from side members 24a and 24b, respectively, in a plane generally parallel to central member 22. Central member 22 has both a top surface 28 and a bottom surface 30 (FIG. 4). Contact between base members 26a and 26b and support surface 90 further help in preventing shifting of protective device 20 and also allow forces applied to top surface 28 of member 22 to be directed away from the patient's face and head through side members 24a and 24b and base members 26a and 26b to support surface 90. Additionally, central member 22, side members 24a and 24b, and base members 26a and 26b help prevent the patient's head from falling sideways, potentially decreasing the blood flow through the neck veins and arteries and leading to nerve damage.

Top surface 28 of member 22 is generally flat, providing a surface on which to rest surgical instruments or devices. Protective device 20 is sized whereby bottom surface 30 makes light contact with or is just above the patient's face. Member 22 may include one or more openings or apertures for various facial structures. In the illustrated embodiment, central member 22 has a generally rectangular aperture 34 for the mouth and a generally T-shaped aperture 36 for the nose and eyes, with the apertures 34, 36 being separated by a bridge portion 39 that is located over the individual's upper lip when protective device 20 is positioned about the patient's head. Apertures for other structures such as the patient's ears are also envisioned. Apertures 34 and 36 not only permit bottom surface 30 of central member 22 to make light contact with the patient's face, they also provide easy access to the eyes, nose, and mouth during surgery. Optionally, protective device 20 may further include a transparent eye covering or goggles 38 built in or attached to aperture 36 to offer additional protection for the patient's eyes while still allowing the anesthesia provider to easily view and monitor the patient's condition throughout the procedure.

Figure 2:
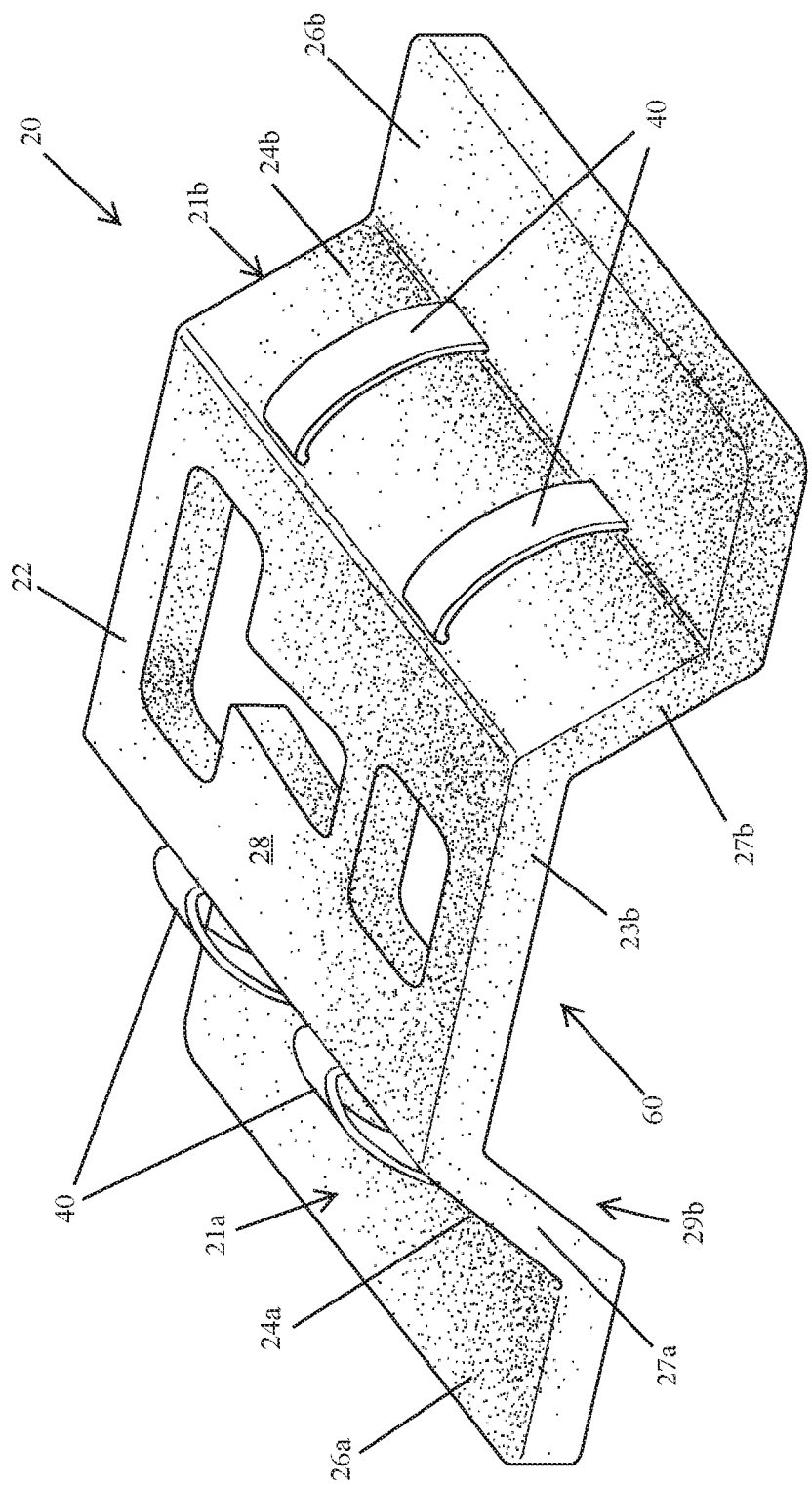
FIG. 2 is a front-right perspective view of the protective device of FIG. 1 shown without the patient.

With reference to FIGS. 1 and 7, member 22 includes upper edge 23a and side members 24a, 24b include upper edges 25a, 25b, respectively. Similarly, with reference to FIGS. 2 and 8, member 22 includes a lower edge 23b and side members 24a, 24b include lower edges 27a, 27b, respectively. Upper edges 23a, 25a and 25b define an upper opening 29a to cavity 60, and lower edges 27a, 23b and 27b define a lower opening 29b to cavity 60. As understood from FIG. 1, when in use upper opening 29a exposes the top of the individual's head, with lower opening 29b being disposed about the individual's neck.

On each side of protective device 20 may be one or more retaining members 40, which may be used to attach various devices and instruments such as an anesthesia circuit 50 or the like. Securing anesthesia circuit 50 to protective device 20 helps to stabilize circuit 50 and protect against unwanted kinking in the tubing, which can lead to inaccurate readings for the anesthesia provider. Retention members 40 on both sides of protective device 20 allow the anesthesia provider to easily secure anesthesia circuit 50 to either the left or right side of the patient. In the illustrated embodiment retention members 40 are constructed as hook and loop fastening mechanisms or straps that are attached to protective device 20 at side members 24a and 24b and base members 26a and 26b through a plurality of slots 42. However, it is envisioned that devices and instruments may be attached to protective device 20 at any number of locations and through any number of means such as, for example, tape, adhesive, or the like. One skilled in the art will recognize and appreciate the various ways devices and instruments may be attached to protective device 20.

Protective device 20 is shown in FIG. 1 with an optional protrusion or holding member 44 affixed to member 22, with holding member 44 being positioned near the mouth aperture 34 for holding or retaining an endotracheal tube 52 inserted into the patient's mouth. Optionally, holding member 44 may be releasably attached to central member 22 such as, for example, through a hook and loop attachment so that holding member 44 may be moved by the anesthesia provider to either side of the patient's mouth and reattached. As shown, holding member 44 has a through-hole 46 that serves as the attachment mechanism for endotracheal tube 52. Optionally, the attachment mechanism for endotracheal tube 52 may take any number of forms, such as a press-fit slot, while remaining within the spirit and scope of the present invention.

In operation, protective device 20 is aligned so apertures 34 and 36 are generally over the appropriate facial structures of the patient. Protective device 20 is then placed over the patient's face so base members 26a and 26b make contact with support surface 90 on each side of the patient's head.

Optionally, if protective device 20 is so equipped, transparent goggles 38 may be placed over the patient's eyes and anesthesia circuit 50 and endotracheal tube 52 may be secured to either the left or right side of protective device 20 through the use of retaining members 40 and/or holding member 44.

In the embodiment shown, central member 22, side members 24a and 24b, and base members 26a and 26b are each generally rectangular in shape. Side members 24a, 24b each have planar top surfaces 31a, 31b (FIG. 3) and bottom surfaces 33a, 33b (FIG. 4). Base members 24a, 24b each have planar top surfaces 35a, 35b (FIG. 3) and bottom surfaces 37a, 37b (FIG. 4). Side members 24a, 24b are connected to member 22 at angled joints 43a and 43b (FIG. 8), respectively. Side members 24a, 24b are also connected to base members 26a, 26b at angled joints 45a and 45b (FIG. 8), respectively. In the illustrated embodiment the internal surfaces of member 22 and side members 24a, 24b at joints 43a, 43b define obtuse angles 47a and 47b (FIG. 8), respectively, and the exterior surfaces of side members 24a, 24b relative to base members 26a, 26b at joints 45a, 45b also define obtuse angles 48a and 48b (FIG. 8), respectively. Also in the illustrated embodiment, the overall length 70 (FIG. 3) of protective device 20 is approximately 10 inches, with member 22 having a width 72 (FIG. 3) of approximately 10 inches. Base members 26a and 26b have widths 74a and 74b (FIG. 3), respectively, measuring about 5 inches. Side members 24a and 24b extend downward from opposite sides of central member 22 to base members 26a and 26b defining cavity 60 having a depth 78 (FIG. 8) of approximately 6 inches. It should be appreciated, however, that alternative shapes and sizes may be employed. For example, the size of central member 22 and depth 78 of cavity 60 may vary to accommodate the different physical sizes of patients' heads.

Figure 3:
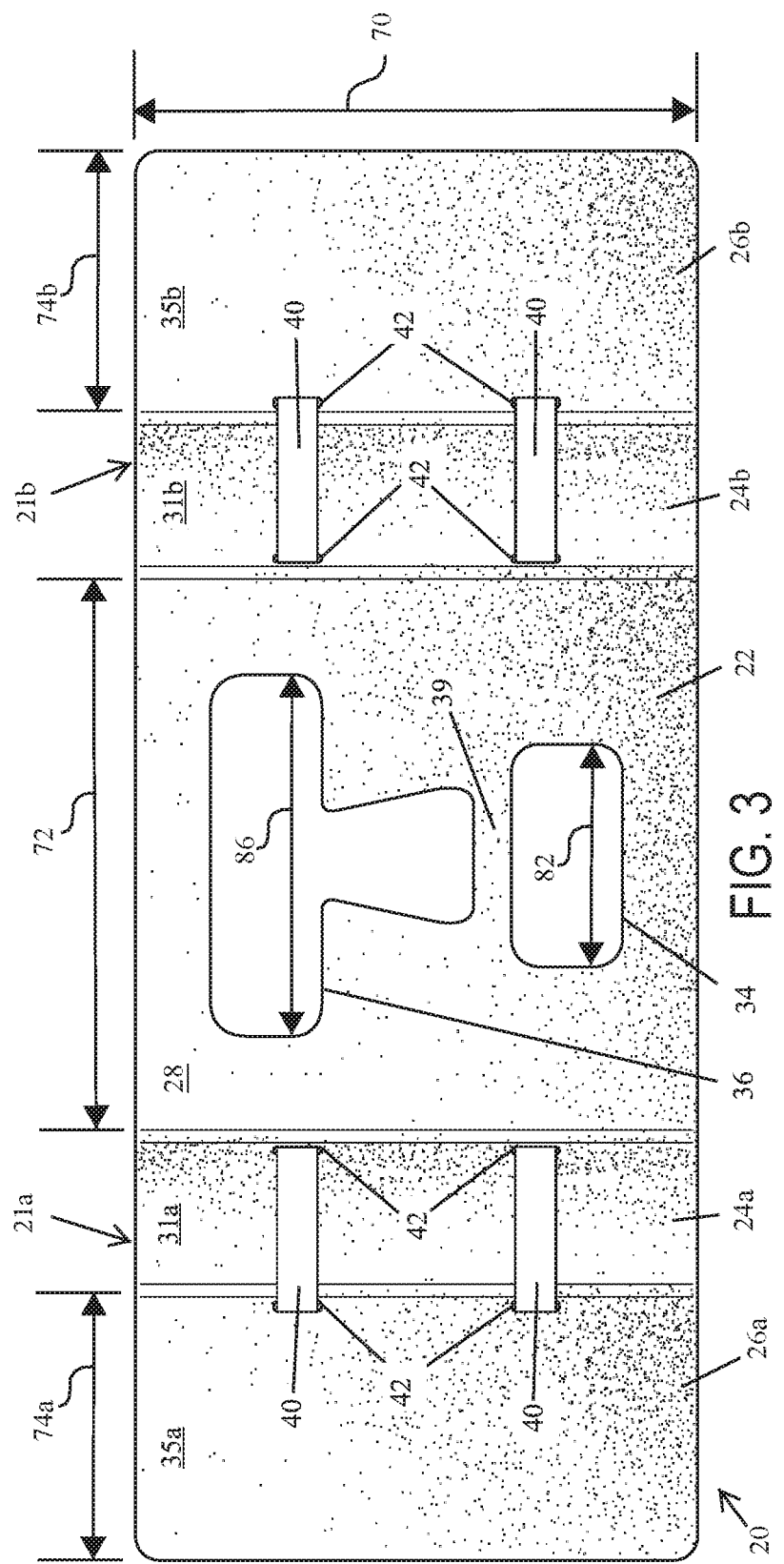
FIG. 3 is a top plan view of the protective device of FIG. 2.
Figure 10:
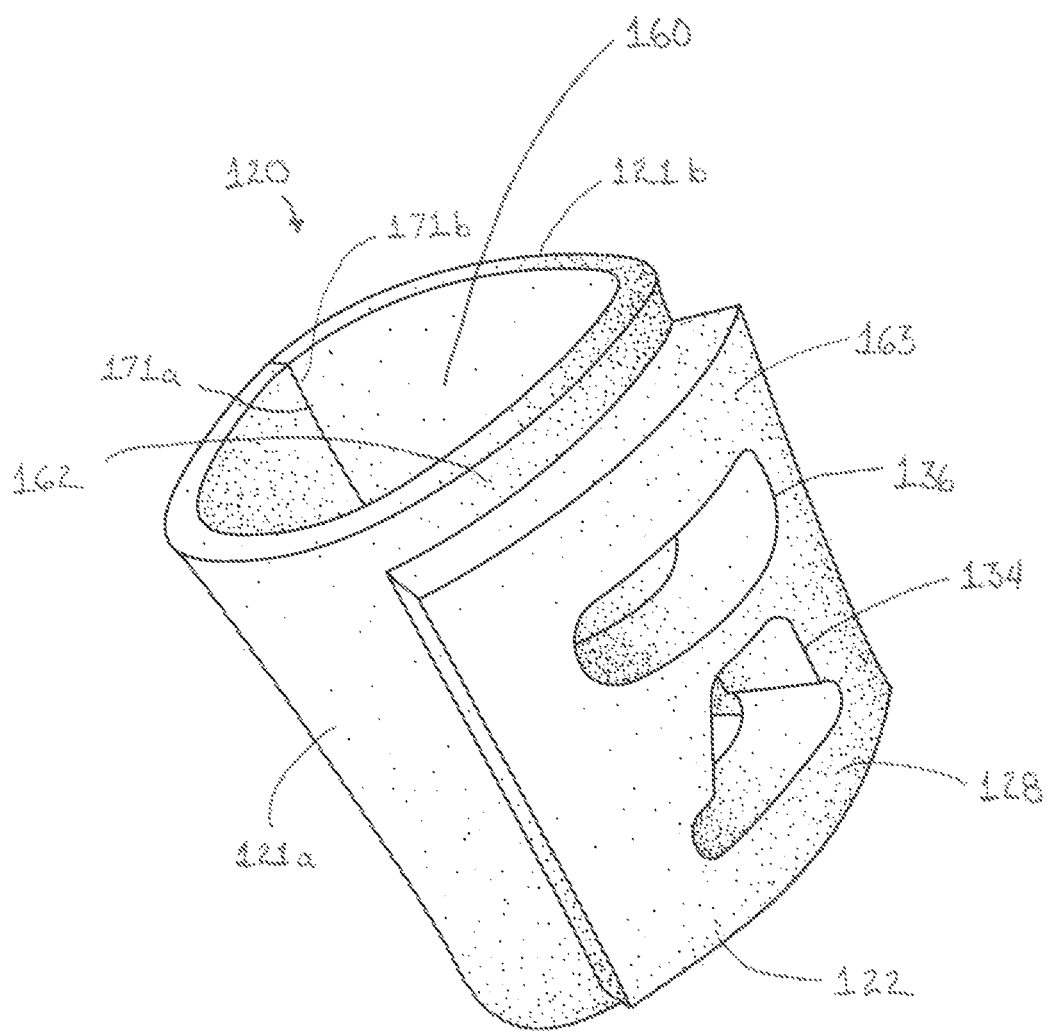
FIG. 10 is a side-perspective view of the protective device of FIG. 9 shown removed from the patient.
Figure 11:
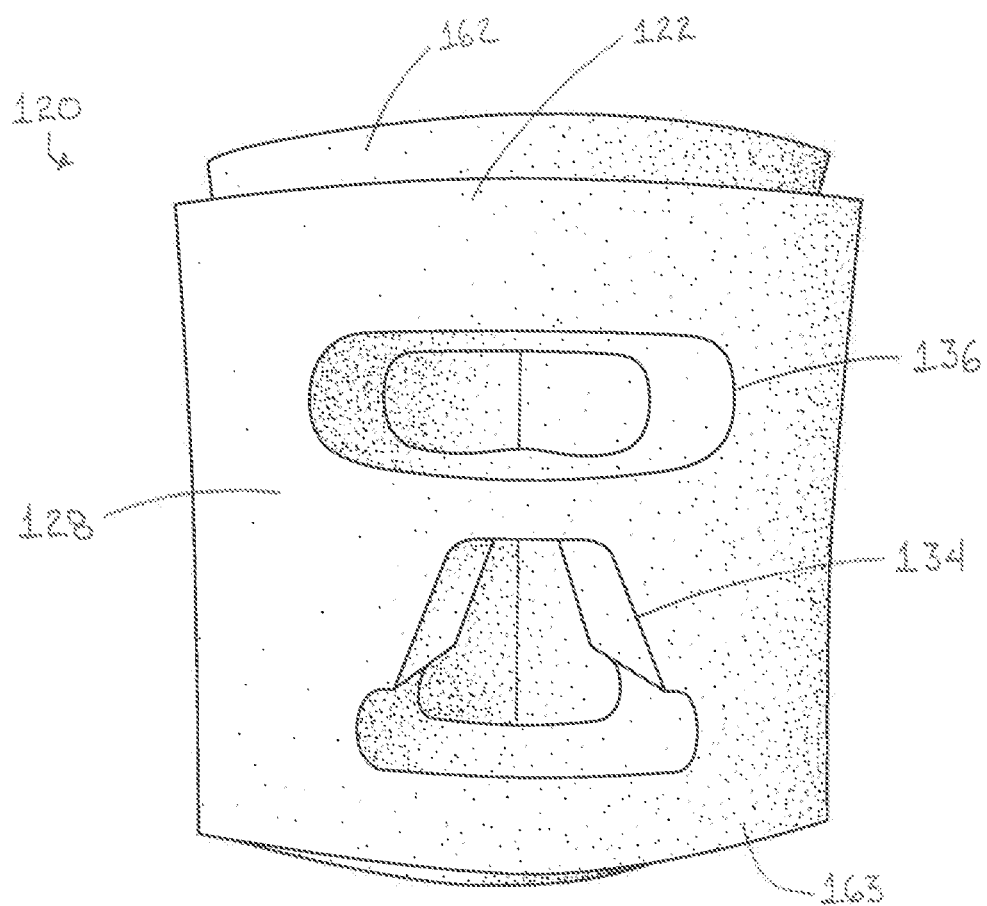
FIG. 11 is a front-perspective view of the protective device of FIG. 10.
Figure 12:
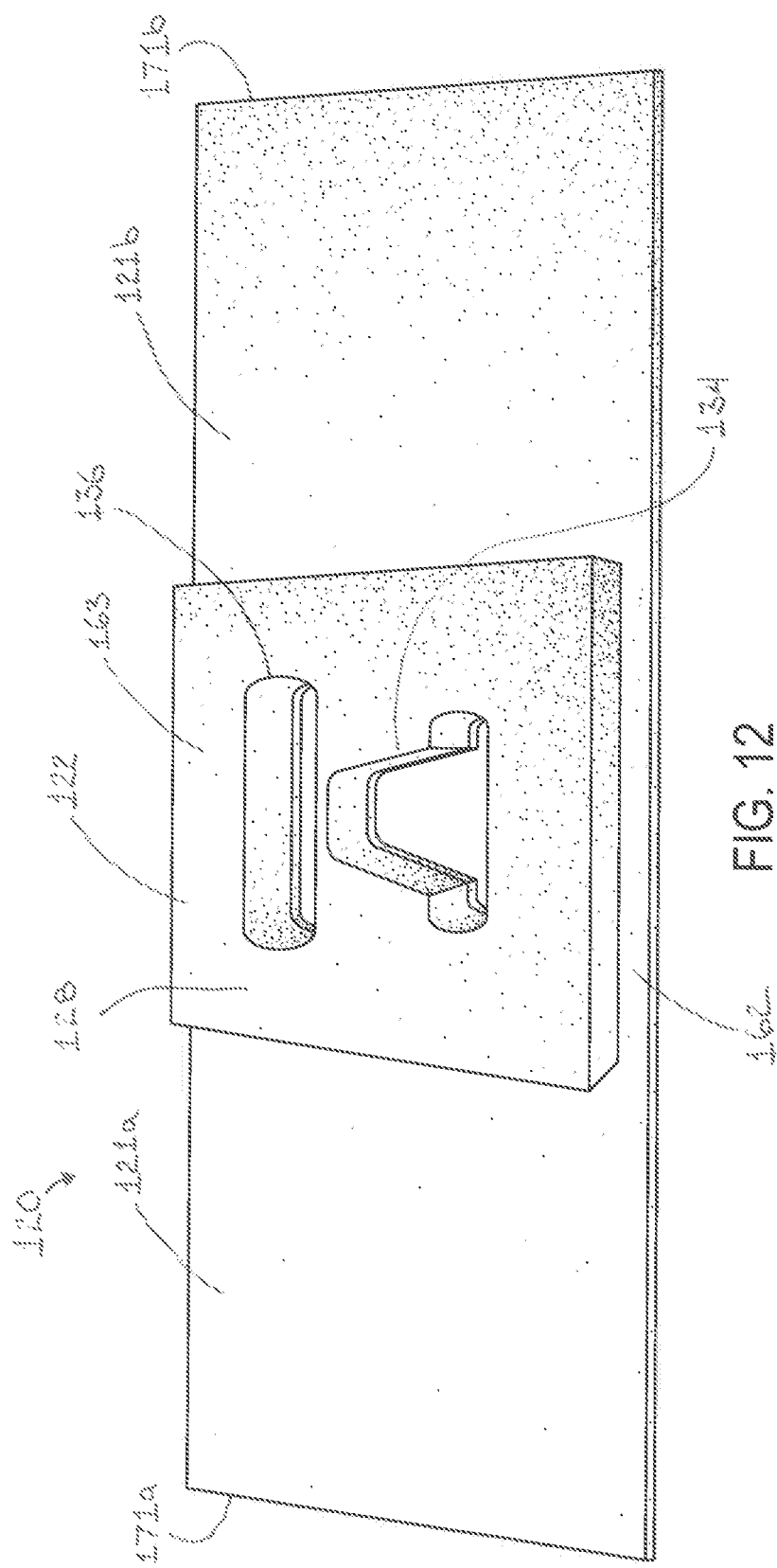
FIG. 12 is a front-perspective view of the protective device of FIG. 10 shown in an unwrapped orientation.

Referring now to FIGS. 3 and 4, central member 22 is shown having two apertures 34 and 36. Aperture 34 is positioned to generally align with the patient's mouth and aperture 36 is positioned to generally align with the patient's nose and eyes. Aperture 34 is essentially rectangular in shape having a height 80 of approximately 2 inches and a width 82 of approximately 4 inches. Aperture 36 is generally T-shaped with the opening for the eyes having a height 84 of about 2 inches and a width 86 of about 6.5 inches. The opening for the nose has a height 88 of approximately 4.3 inches. Such sizes are selected to accommodate variations in facial dimensions. However, it should be recognized that alternative shapes, sizes, and number of apertures may be employed.

In the illustrated embodiment, protective device 20 is formed by a molding process with central member 22, side members 24a and 24b, and base members 26a and 26b comprising a unitary piece of a soft, solid foam material to provide cushioned protection for the face and cranial region of the patient. Such material is light weight and easy to cut in order to gain access to the face. Additionally, such material is generally inexpensive, so protective device 20 may be disposed of after each individual use, avoiding the need to sterilize device 20 between uses. It should be appreciated, however, that protective device 20 may be formed from foam material of varying degrees of rigidity or may be constructed from any suitable light weight material, such as a plastic or polymeric material or the like, capable of providing protection for the face and cranial region of the patient. Further, as an alternative to single piece construction, protective device 20 may optionally be assembled from two or more pieces fixedly attached to each other.

In the illustrated embodiment, base elements 26a and 26b extend outward and away from side members 24a and 26b, respectively, forming a planar surface generally parallel to central member 22. It is envisioned, however, that base elements do not have to extend outward from side members 24a and 24b, but rather may be the bottom ends of side members 24a and 24b. The base elements still lie in generally in a plane parallel to central member 22 and make contact with support surface 90 to allow forces applied to top surface 28 of central member 22 to be directed to support surface 90.

Referring now to the embodiment of FIGS. 9-15, an alternative facial and head protective device 120 is disclosed positioned on patient 15, where patient 15 is shown in the supine position on support surface 190 with anesthesia circuit 150 provided to patient 15. In like manner to protective device 20, protective device 120 supports and protects the face of patient 15 during a medical procedure, as well as operates to keep the patient warm, as discussed below. Protective device 120 shares similar features and components with protective device 20, with related features being shown in FIGS. 9-15 with similar reference numerals, but with 100 added to the reference numerals relative to the reference numerals of device 20.

Protective device 120 includes a face portion or central member 122 with a pair of side portions 121a, 121b extending in opposite directions from face portion 122. In the illustrated embodiment, face portion 122 is constructed of a first or base layer 162 and a second or top layer 163 disposed on and connected to base layer 162, such as by an adhesive or the like. Base layer 162 is constructed of a fire retardant polyurethane memory foam to provide a gentle cushioning material to the face of the patient. Top layer 163 is also made of a fire retardant polyurethane foam, but is stiffer or firmer than base layer 162 to provide resistance to pressure. That is, the top layer 163 is more resistant to bending or deformation. Apertures 134, 136 are provided through top layer 163 and base layer 162, with aperture 136 configured for positioning about the eyes of the patient 15, and aperture 134 configured for positioning about the mouth and nose of the patient 15. Anesthesia circuit 150 is provided to patient 15 through aperture 134, and may be taped to protective device 120 to aid in retention.

In the illustrated embodiment side portions 121a, 121b are unitarily formed with base layer 162 of face portion 122 and have approximately equal lengths to extend approximately equally from face portion 122 in opposite directions. That is, a single member or portion or layer of foam forms both the side portions 121a, 121b and the base layer 162 of face portion 122. Side portions 121a, 121b are flexible and sized to extend from face portion 122 a sufficient distance to enable the side portions 121a, 121b to be wrapped around the head of the patient 15. Side portions 121a, 121b include elongate ends 171a, 171b, respectively, that are placed into abutting engagement with one another when positioned around the head of the patient 15 (FIG. 10) to form a cavity 160 for receiving the patient's head. When so positioned, the side portions 121a, 121b can be taped together to retain the protective device 120 in position. It should be appreciated that alternatively, depending on required sizes and/or the sizes of side portions 121a, 121b, that the ends 171a, 171b may overlap with one another. It should also be appreciated that the lengths of side portions 121a, 121b may be trimmed as needed for a given patient, or alternative joining techniques may be employed, such as hook and loop fastener connections or the like.

The wrapping of the side portions 121a, 121b about the head of the patient 15 aid in retaining the protective device 120 in position, as well as beneficially assist in keeping the patient 15 warm during a procedure. In the illustrated embodiment side portions 121a, 121b have a thickness of approximately 0.5 inches, a width of approximately 10 inches, with protective device 120 having an overall length of approximately 34 inches from end 171a to end 171b when in the position of FIG. 13. Also in the illustrated embodiment, top layer 163 has a thickness of approximately 1.25 inches and a length of approximately 7.75 inches. Aperture 136 is approximately 4.75 inches long and 1.25 inches wide, with aperture 134 being approximately 3.75 inches long at the lower base and approximately one inch wide about the mouth, with angled sides that are approximately two inches in length extending about the nose location.

The apparatuses and methods of the present invention provide protection for a patient undergoing surgery in the supine position by allowing forces to be directed away from the sensitive areas of the face and cranial region. The apparatus and method of the present invention also help to keep the patient's head from falling to the side, further reducing the risks of decreased blood flow and possible nerve damage. The apparatus and method, therefore, provide increased protection over conventional practices.

Changes and modifications to the specifically described embodiments may be carried out without departing from the principles of the present invention, which is intended to be limited only by the scope of the appended claims as interpreted according to the principles of patent law including the doctrine of equivalents.

The embodiments of the invention in which an exclusive property or privilege is claimed are defined as follows:

1. A protective device for protecting the face and/or head of an individual receiving medical treatment in a face upward position, said protective device comprising:
   a face portion comprising a top layer and a separate base layer that are constructed of foam and affixed together, said face portion having an exterior surface on said top layer, an interior surface on said base layer, and an aperture extending through said top layer and said base layer from said exterior surface to said interior surface, wherein said face portion is configured to be positioned over the face of the individual with at least a portion of the individual's face exposed by said aperture;
   a pair of opposed flexible side portions defined by said base layer and extending outwardly from said face portion, said side portions extending beyond said top layer and configured to being brought into engagement with each other whereby said face portion and said side portions define a cavity and a pair of openings to said cavity, and wherein said side portions are configured to encircle the head of the individual whereby the individual's head is supported on at least one of said side portions when the individual is receiving medical treatment in a face upward position, and wherein said top layer is configured to not wrap around sides of the individual's head;
   wherein said protective device is configured to be disposed about the head of the individual with the individual's head disposed within said cavity and a top of the individual's head exposed by one of said openings.

2. The protective device of claim 1, wherein said protective device defines a generally rectangular shape when said side portions are not in engagement with each other.

3. The protective device of claim 2, wherein said side portions and said face portion of said base layer comprise a unitary member formed of the same material.

4. The protective device of claim 1, wherein said top layer is constructed of a first foam and said base layer is constructed of a second foam, and wherein said first foam is stiffer than said second foam.

5. The protective device of claim 1, wherein said top layer is thicker than said base layer.

6. The protective device of claim 5, wherein said top layer is at least approximately twice as thick as said base layer.

7. The protective device of claim 1, wherein said top layer is adhesively affixed to said base layer.

8. The protective device of claim 1, wherein said side portions each include an end, and wherein said ends engage with each other when said side portions are wrapped about the head of an individual.

9. The protective device of claim 1, wherein said side portions are of substantially similar length with respect to each other.

10. The protective device of claim 1, wherein said aperture comprises a pair of apertures, and wherein one said aperture is configured to expose the individual's eyes and the other said aperture is configured to expose the individual's nose and mouth.

11. A protective device for protecting the face and/or head of an individual receiving medical treatment in a face upward position, said protective device comprising:
   a face portion comprising a top layer and a separate base layer that are affixed together and having an exterior surface on said top layer, an interior surface on said base layer, and an aperture extending through said top layer and said base layer from said exterior surface to said interior surface, wherein said face portion is configured to be positioned over the face of the individual with at least a portion of the individual's face exposed by said aperture;
   a pair of opposed flexible side portions defined by said base portion and extending outwardly from said face portion, said side portions extending beyond said top layer and configured to being brought into engagement with each other whereby said face portion and said side portions define a cavity and a pair of openings to said cavity, and wherein said side portions are configured to encircle the head of the individual whereby the individual's head is supported on at least one of said side portions when the individual is receiving medical treatment in a face upward position, and wherein said top layer is configured to not wrap around sides of the individual's head;
   wherein said protective device is configured to be disposed about the head of the individual with the individual's head disposed within said cavity and a top of the individual's head exposed by one of said openings; and
   wherein said top layer and said base layer are constructed of foam, and wherein said side portions and said base layer comprise a unitary member formed of the same material.

12. The protective device of claim 11, wherein said top layer is constructed of a first foam and said base layer is constructed of a second foam, and wherein said first foam is stiffer than said second foam.

13. The protective device of claim 11, wherein said top layer is thicker than said base layer.

14. The protective device of claim 13, wherein said top layer is at least approximately twice as thick as said base layer.

15. The protective device of claim 11, wherein said side portions each include an end, and wherein said ends engage with each other when said side portions are wrapped about the head of an individual.

16. The protective device of claim 11, wherein said side portions are of substantially similar length with respect to each other.

17. The protective device of claim 11, wherein said aperture comprises a pair of apertures, and wherein one said aperture is configured to expose the individual's eyes and the other said aperture is configured to expose the individual's nose and mouth.

18. A method of protecting the face and/or head of an individual receiving medical treatment in a face upward position, said method comprising:
   providing a protective device, said protective device comprising a face portion comprising a top layer and a separate base layer that are affixed together, said face portion having an exterior surface on said top layer, an interior surface on said base layer, and an aperture extending through said top layer and said base layer from said exterior surface to said interior surface, said protective device further comprising a pair of opposed flexible side portions defined by said base layer and extending outwardly from said face portion, said side portions extending beyond said top layer and configured to being brought into engagement with each other whereby said face portion and said side portions define a cavity having a pair of openings to said cavity;
   positioning said face portion over the face of the individual with at least a portion of the individual's face exposed by said aperture; and
   wrapping said side portions around the head of the individual to encircle the head of the individual whereby the individual's head is disposed within said cavity and supported on at least one of the side portions when the individual is receiving medical treatment in a face upward position with a top of the individual's head being exposed by one of said openings and wherein said top layer is configured to not wrap around the sides of the individual's head.

19. The method of claim 18, wherein said face portion of said protective device comprises a top layer and a separate base layer with said side portions and said base layer comprising a unitary member formed of the same material, and wherein said top layer and said base layer are constructed of foam with said top layer being stiffer than said base layer.

* * * * *